United States Patent [19]

Link, Jr. et al.

[11] Patent Number: 5,985,266
[45] Date of Patent: Nov. 16, 1999

[54] RADIATION ENHANCED THERAPY FOR TUMORS EXPRESSING A GENE FOR VIRAL THYMIDINE KINASE IN THE PRESENCE OF A 5-HALOGENGATED PYRIMIDINE

[75] Inventors: Charles J. Link, Jr., Des Moines, Iowa; Sheldon B. Greer, North Miami Beach, Fla.

[73] Assignee: Human Gene Therapy Research Institute, Des Moines, Iowa

[21] Appl. No.: 08/903,459

[22] Filed: Jul. 30, 1997

Related U.S. Application Data

[63] Continuation-in-part of application No. 08/396,638, Mar. 1, 1995, abandoned.
[51] Int. Cl.$^6$ .................... A61K 48/00; C12N 15/00
[52] U.S. Cl. ............... 424/93.21; 424/93.2; 514/44; 435/325; 435/320.1
[58] Field of Search ............. 514/44, 49; 424/93.2, 424/93.21; 435/325, 320.1

[56] References Cited

U.S. PATENT DOCUMENTS

| 4,894,364 | 1/1990 | Greer | 514/49 |
| 5,529,774 | 6/1996 | Barba et al. | 424/93.21 |
| 5,631,236 | 5/1997 | Woo | 514/44 |

FOREIGN PATENT DOCUMENTS

| WO 93/04167 | 3/1993 | WIPO | C12N 15/00 |

OTHER PUBLICATIONS

Muller (1994) Pharmac. Ther. 63, 199–207.
Bi, 1993, In Vitro Evidence that Metabolic Cooperation is Responsible for the Bystander Effect Observed with HSV tk Retroviral Gene Therapy, *Human Gene Therapy* 4:725–731.
Borrelli, "Targeting of an Inducible Toxic Phenotype in Animal Cells", *Proc. Natl. Acad. Sci. USA*, vol. 85:7572–7576 (1988).
Caruso, 1993, Regression of Established Macroscopic Liver Metastases After In Situ Transduction of a Suicide Gene, *Proc. Natl. Acad. Sci. USA*, vol. 90:7024–7028.
Chen, 1994, Gene Therapy for Brain Tumors: Regression of Experimental Gliomas by Adenovirus–Mediated Gene Transfer In Vivo, *Proc. Natl. Acad. Sci, USA*, 91:3054–3057.
Cheng, "Metabolism of 9–(1, 3–Dihydroxy–2–Propoxymethyl)guanine, a New Anti–herpes Virus Compound, in Herpes Simplex Virus–Infected Cells", *The Journal of Biological Chemistry*, vol. 258(20):12460–12464 (1983).
Culver, "In Vivo Gene Transfer with Retroviral Vector–Producer Cells for Treatment of Experimental Brain Tumors", *Science*, vol. 256:1550–1552 (1992).
Culver, "Gene Therapy for Cancer", *Trends in Genetics*, vol. 10(5) May 1994.
Elion, "The Chemotherapeutic Exploitation of Virus–Specified Enzymes", *Adv. Enz. Regulation*, 18:53–66 (1980).
Freeman, "The 'Bystander Effect': Tumor Regression When a Fraction of the Tumor Mass is Genetically Modified", *Cancer Research*, 53:5274–5283 (1993).

Goffman, T., "Long–Term Follow–Up on National Cancer Institute Phase I/II Study of Glioblastoma Multiforme Treated With Iododeoxyuridine and Hyperfractionated Irradiation", *J. of Clinical Oncology*, 10(2):264–268 (1992).
Greer, "5–Halogenated Analogs of Deoxycytidine as Selective Inhibitors of the Replication of Herpes Simplex Viruses in Cell Culture and Related Studies of Intracranial Herpes Simplex Virus Infections in Mice", *Annals New York Academy of Sciences*, vol. 255:359–365 (1975).
Harrison, D., "Competitive Repopulation in Unirradiated Normal Recipients", *Blood, J. of The American Society of Hematology*, 81(10):2473–2474 (1993).
Heyman, "Thymidine Kinase Obliteration: Creation of Transgenic Mice with Controlled Immune Deficiency", *Proc. Natl. Acad. Sci. USA*, vol. 86:2698–2702 (1989).
Hodgson, C., "Advances in Vector Systems for Gene Therapy", Patent Update Biologicals & Immunologicals, *Exp. Opin. Ther. Patents* 5(5):459–468 (1995).
Huber, "Retroviral–Mediated Gene Therapy for the Treatment of Hepatocellular carcinola: An Innovative Approach for Cancer Therapy", *Proc. Natl. Acad. Sci. USA*, vol. 88:8039–8043 (1991).
Kim, "Selective Enhancement by an Antiviral Agent of the Radiation–Induced Cell Killing of Human Glioma Cells Transduced with HSV–tk Gene", *Cancer Research* vol. 54:6053–6056 (1994).
Kim, J., "Use of Retroviral Gene Transfer and Antiviral Agents as Radiation Sensitizers in Cultured Brain Tumor Cells", abstract, *Proceedings of American Assoc. for Cancer Research*, 35:637 (1994).
Marshall, E., "Gene Therapy's Growing Pains", *Science*, 269:1050–1055 (1995).
Miller, N., "Targeted Vectors for Gene Therapy", *FASEB Journal*, 9:190–199 (1995).
Mitchell, J., "Radiobiology and Clinical Application of Halogenated Pyrimidine Radiosensitizers", *Int. J. Radiat. Biol.*, 56(5):827–836 (1989).
Moolten, "Tumor Chenosensitivity Conferred by Inserted Herpes Thymidine Kinase Genes: Paradigm for a Prospective Cancer Control Stratety", *Cancer Research*, 46:5276–5281 (1986).
Moolten, "Curability of Tumors Bearing Herpes Thymidine Kinase Genes Transferred by Retroviral Vectors", *Reports*, vol. 82(4):297–300 (1990).
Moolten, "Lymphoma Regression Induced by Ganciclovir in Mice Bearing a Herpes Thymidine Kinase Transgene", *Human Gene Therapy*, 1:125–134 (1990).

(List continued on next page.)

*Primary Examiner*—Deborah Crouch
*Attorney, Agent, or Firm*—Zarley, McKee, Thomte, Voorhees & Sease

[57] ABSTRACT

The present invention pertains to combination radio therapy of tumors and more specifically to pharmaceutical compositions, and methods of treatment by gene therapy designed to sensitize tumors in animals, notably humans, and render them more susceptible to radiation, thus significantly reducing the amount of radiation required to kill neoplastic cells while at the same time making the radiation far more tissue specific to the tumor site.

13 Claims, 4 Drawing Sheets

OTHER PUBLICATIONS

Ohno, Gene Therapy for Vascular Smooth Muscle Cells Proliferation After Arterial Injury, *Science,* vol. 265:781–784 (1994).

Orkin, Report and Recommendations of the Panel to Assess the NIH Investment in Research on Gene Therapy (1995).

Plautz, "Selective Elimination of Recombinant Genes In Vivo with a Suicide Retroviral Vector", *The New Biologist,* vol. 3(7):709–715 (1991).

Ram, 1993, In Situ Retroviral–Mediated Gene Transfer for the Treatment of Brain Tumors in Rats, *Cancer Research,* 53:83–88.

Ram, 1993, Toxicity Studies of Retroviral–Mediated Gene Transfer for the Treatment of Brain Tumors, *J. Neurosurg.,* vol. 79:400–407.

Ram, "In Vivo Transfer of the Human Interleukin–2 Gene: Negative Tumoricidal Results in Experimental Brain Tumors", *J. Neurosurg.* 80:535–540 (1994).

Ram, "Gene Therapy for Malignant Brain Tumors: Preliminary Results of a Clinical Study", Surgical Neurology Branch, NINDS, NIH, Bethesda, MD.

Takamiya, "An Experimental Model of Retrovirus Gene Therapy for Malignant Brain Tumors", *J. Neurosurg.* 79:104–110, 1993.

Vile, "Use of Tissue–Specific Expression of the Herpes Simplex Virus Thymidine Kinase Gene to Inhibit Growth of Established Murine Melanomas Following Direct Intratumoral Injection of DNA", *Cancer Research* 53:3860–3864 (1993).

Weichselbaum, "Gene Therapy Targeted by Ionizing Radiation", *International Journal of Radiation Oncology Biology Physics,* vol 24:565–567 (1992).

RADIATION ENHANCED THERAPY FOR TUMORS EXPRESSING A GENE FOR VIRAL THYMIDINE KINASE IN THE PRESENCE OF A 5-HALOGENGATED PYRIMIDINE

This application is a continuation-in-part application of U.S. patent application Ser. No. 08/396,638 filed Mar. 1, 1995 now abandoned.

BACKGROUND OF THE INVENTION

The present invention pertains to combination radiotherapy of tumors and more specifically to pharmaceutical compositions, and methods of treatment by gene therapy designed to sensitize tumors in animals, notably humans, and render them more susceptible to radiation, thus significantly reducing the amount of radiation required to kill neoplastic cells while at the same time making the radiation far more tissue specific to the tumor site.

The limited ability of anti-neoplastic therapy to distinguish neoplastic from normal cells on the basis of proliferative behavior has inspired a search for biochemical characteristics of neoplastic cells that are tumor specific rather than proliferation specific. Unfortunately current molecular genetic studies have failed to support the expectation that such characteristics are a consistent feature of neoplastic cells. Rather these studies suggest that the neoplastic state can be explained without postulating tumor specific functions, but merely the operation of normal proliferation-specific functions at abnormal levels, as a result of changes (sometimes minimal) in the structure of growth-regulatory genes or changes in their number or chromosomal environment. This conclusion suggests that a continued search for highly specific attributes of neoplastic cells cannot be relied upon for a general solution to the problems of cancer therapy. Major reductions in the lethality of cancer will require alternative approaches that do not depend on the natural occurrence of such attributes.

One alternative strategy entails the artificial creation of differences between normal and neoplastic cells through prophylactic use of gene insertion techniques. In other words, manufacturing biochemical differences which can be exploited to systematically and specifically target neoplastic cells for destruction. This invention involves combination gene therapy and radiation treatment to inhibit proliferation and kill neoplastic cells. Gene insertion protocols are used to artificially manufacture biochemical differences in target tumor cells which are then exploited to sensitize the cells to the effects of radiation.

Thus an object of the present invention is to provide therapeutic materials and procedures for treating tumors using, for example, ultraviolet light, near visible light (313 nm), x, gamma, β, πmeson, neutron, or other radiation entities.

Another object of the invention is to sensitize tumor cells to radiation using gene therapy to engineer biochemical differences in tumor cells which are exploited to confer sensitivity to the effects of radiation therapy.

SUMMARY OF THE INVENTION

This invention pertains generally to the introduction of genes to tumor cells to modify a drug that acts as a radiosensitizer. In one embodiment, it is postulated that certain CMV or thymidine kinase-activated nucleoside analogues derived from either purine or pyrimidine building blocks, can be potent radiation sensitizers to transformed mammalian cells, such that the addition of radiation therapy may provide an additive or synergistic benefit. The viral thymidine kinase allows activation of drugs (e.g. pyrimidine nucleoside analogs) which are not (or poorly) activated in cells containing cellular thymidine or deoxycytidine kinase. This allows for selective radiosensitization of cells containing viral thymidine kinase by gene manipulation when certain analogs which are precursors to radiosensitizers are utilized.

Applicant's invention represents the first demonstration of selective enhancement of radiation sensitivity by proliferating cancer cells using a gene therapy approach. The selective cytotoxicity of the antiviral drug ganciclovir on tumor tissue has been demonstrated previously, but it would be extremely difficult to achieve a complete erradication of locally advanced tumors with the antiviral drug alone. According to the present invention, further selective cytotoxicity can be achieved with the addition of radiation and the use of agents which are not merely antiviral agents, but those which are precursors to true radiosensitizers.

DETAILED DESCRIPTION OF THE INVENTION

Figure 1:
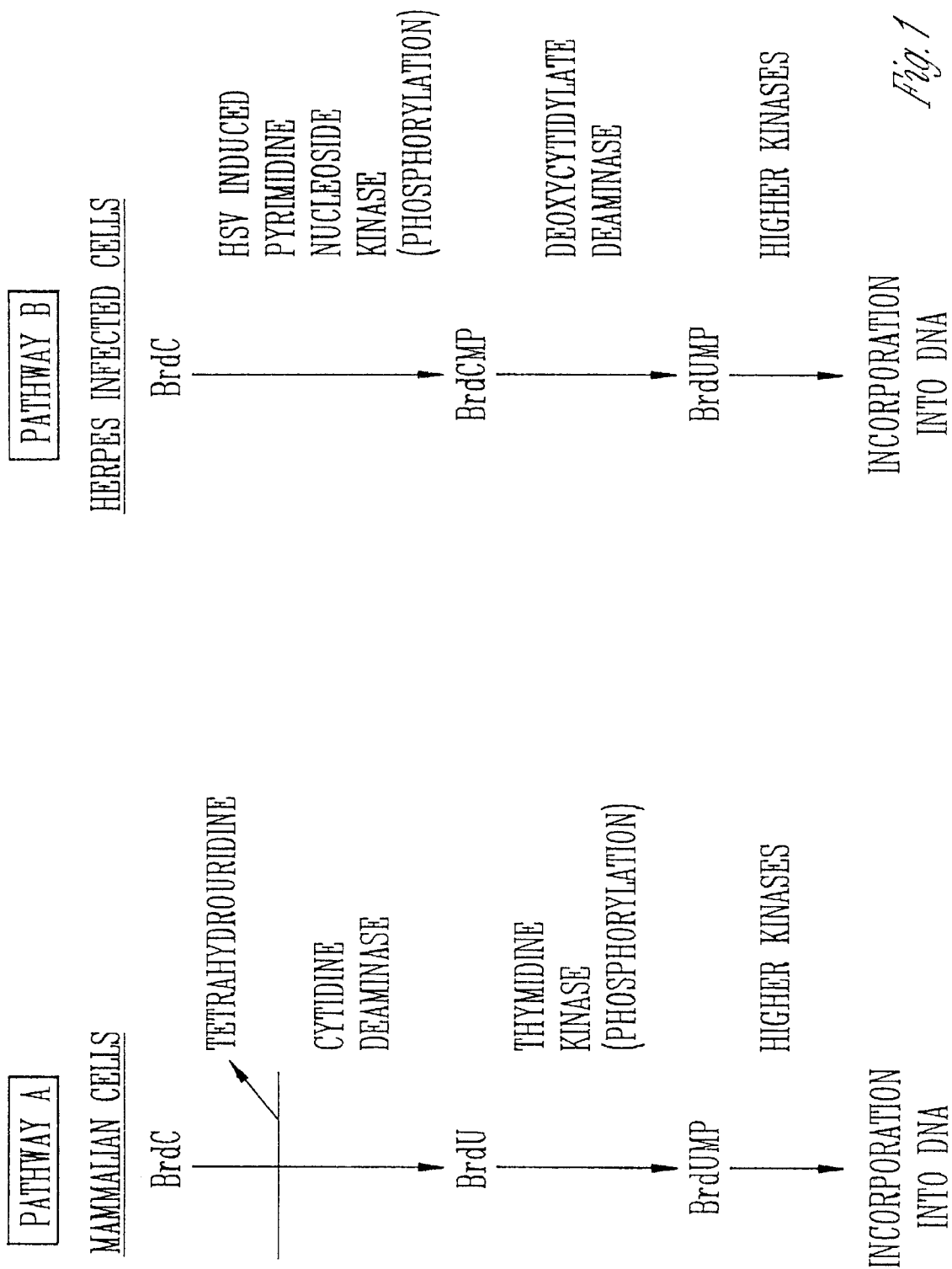
FIG. 1 is a depiction of the pathways of metabolism of 5-bromodeoxycytidine in mammalian cells (pathway A) and the additional pathway present in Herpes thymidine kinase transfromed cells. (Pathway B). As used in the Figure and throughout the following application the following abbreivieations are disclosed: 5-bromo-2'-deoxycytidine (BrdC); 5-iodo-2'-deoxycytidine (IdC); 5-Bromo-2'-deoxyuridine (BrdU); 5-iodo-2'-deoxyuridine (IdU); 5-Bromo-2'-deoxyuridine 5' monophosphate (BrdUMP) 5-Iododeoxyuridine-5' monophosphate (IdUMP); 5-Bromodeoxycytidine-5' monophosphate (BrdCMP) 5-Iododeoxycytidine-5'.

Many radiation sensitizers which have shown considerable potential in vitro have been found to be limited in clinical effectiveness primarily because of normal tissue toxicity. Conventional radiation sensitizers operate by one of two strategies, they either modify the structure of DNA to make it more sensitive to the action of radiation by resulting in excessive DNA strand breaks or they inhibit repair of DNA lesions produced by radiation. Halogenated uridine derivatives such as bromodeoxyuridine have been proposed to function by the former mechanism since they must be present prior to radiation to be effective. These analogs must be present prior to irradiation because they must be incorporated into DNA to display radiosensitization. It is thought that a secondary effect of their administration may be the inhibition of repair by nuclioside pool imbalances and that DNA containing these analogs is a poor substrate for repair enzymes. Results of clinical studies, however, involving bromodeoxyuridine infusion and radiation treatment for brain tumors and tumors of the head and neck have been disappointing due to the dose-limiting toxicity of proliferating normal tissues, bone marrow and intestines.

If the drug is to be an effective radiation sensitizer by the latter mechanism by inhibiting the repair of DNA lesions, it must be present at the time after radiation. Several nucleoside analogues, well known anti viral agents including 1-β-D-arabinofuranosyladenine, 1-β-D-arabinofuranosylcytosine, and acyclovir have been shown to increase the cytotoxicity of radiation exposure. Unfortunately at the drug concentrations that need to be achieved in humans, such anti-Herpetic agents have not been found to be effective radiation sensitizers in in vivo systems studied to date.

Applicants invention solves this problem of normal tissue toxicity due to nonspecific action. The invention, comprising gene-activated radiation enhancement, reduces normal tissue complication to negligible levels. To date there has been one attempt to combine radiation with gene therapy protocols, Wechselbaum et al demonstrated the feasibility of upregulating tumor necrosis factor expression following exposure to large doses of radiation. Wechselbaum et al., Int. J. Radiation Oncology, Biol. Phys., 24, pages 565, 567 (1992). Wechselbaum and colleagues proposed a possibility of regulating transcription of genes encoding cytotoxic proteins by placing radiation response elements in front of genetic constructs which may activate or amplify radiation induced signals or genes that encode proteins which increase radiation tolerance of dose limiting normal tissues. See Wechselbaum et al. "Gene Therapy Targeted by Ionizing Radiation" incorporated herein by reference. This is quite different from applicant's invention which comprises use of compounds which are selectively metabolized in Herpes transformed cells to radiation sensitizers.

Internally delivered radiation includes therapeutically effective radioisotopes injected into a patient. Such radioisotopes include but are not limited to: the radio nuclide metals $^{186}$RE, $^{188}$RE, $^{64}$Cu, $^{67}$Cu, $^{90}$ytrium, $^{109}$Pd, $^{212}$Bi, $^{203}$PB, $^{212}$Pb, $^{211}$At, $^{97}$Ru, $^{105}$Rh, $^{198}$Au, $^{199}$Ag, and $^{131}$I. These radioisotopes generally will be bound to carrier molecules (e.g., are in the form of a chelate-antibody conjugate) when administered to a patient. Examples of suitable internally delivered radio therapeutic agents are the metal radio nuclide chelates which are conjugated to antibodies as described in European patent application publication number 199,256. Radiation administered by external means includes external beam radiation such as cobalt therapy and can include other forms of ioninzing radiation such as X-rays, γ-rays, β-rays, ultraviolet light, near ultraviolet light and other sources of radiation including, for example π-mesons. Examples of traditional drugs which have been reported to sensitize cells to therapeutic radiation include those in U.S. Pat. No. 4,628,047 reports use of diltiazem (chemical name: d-3-aceotxy-cis-2,3-dihydro-5-[2-(dimethylamino)ethyl[-2-(p-methoxyphenyl]-1,5-benzothiazepin-4(5H)-1) to enhance the sensitivity of a variety of types of cancer cells toward cytotoxic agents such as doxorubicin.

Applicant's invention involves novel radiation sensitizing agents (precursors) that are safe and non-toxic in normal cells but which are selectively metabolized to active radiation sensitizers in virus transformed cells. One aspect of the invention includes pharmaceutical compositions which may be used in combination with gene therapy for sensitizing transformed cells to radiation therapy. The pharmaceutical compositions of the invention comprise 5-halogenated derivatives of deoxycytidine or derivatives thereof having the following formula:

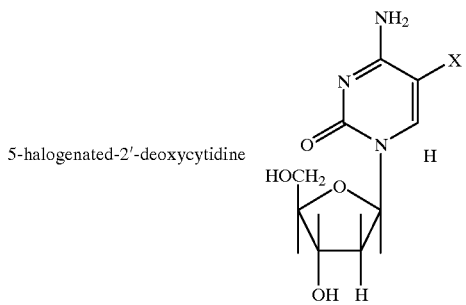

5-halogenated-2'-deoxycytidine

Wherein X is a halogen such as chlorine, fluorine, bromine, or iodine.

For such administration the radiation sensitizer precursor or conjugate thereof can be combined with a pharmaceutically acceptable carrier such as a suitable liquid vehicle or excipient and an optional auxiliary additive or additives. The liquid vehicles and excipients are conventional and are commercially available. Illustrative thereof are distilled water, physiological saline, aqueous solutions of dextrose and the like. Traditionally IV therapy is preferred.

In general, in addition to the active compounds, the pharmaceutical compositions of this invention may contain suitable excipients and auxiliaries which facilitate processing of the active compounds into preparations which can be used pharmaceutically. Oral dosage forms encompass tablets, dragees, and capsules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffinhydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, include for example, sodium carboxymethyl cellulose, sorbitol and/or dextran, optionally the suspension may also contain stabilizers.

In addition to administration with conventional carriers, active ingredients may be administered by a variety of specialized delivery drug techniques which are known to those of skill in the art, such as portable infusion pumps.

In accordance with an aspect of the present invention, there is provided a method of treating a tumor in a human host. The method comprises transducing tumor cells in vivo or in vitro with a nucleic acid (DNA or RNA) sequence encoding an agent which is capable of providing for the inhibition, prevention, or destruction of the growth of the tumor cells upon expression of the nucleic acid sequence encoding the agent and subsequent radiation therapy.

The nucleic acid sequence which encodes the agent which is capable of providing for the inhibition, prevention, or destruction of the growth of the tumor cells is contained in an appropriate expression vehicle which transduces the tumor cells. Such expression vectors include, but are not limited to, eukaryotic vectors, prokaryotic vectors (such as, for example, bacterial vectors), and viral vectors.

In one embodiment, the expression vector is a viral vector. Viral vectors which may be employed include, but are not limited to, retroviral vectors, adenovirus vectors, and adeno-associated virus vectors.

In a preferred embodiment, a packaging cell line is transduced with a viral vector containing the nucleic acid sequence encoding the agent or factor which provides for the inhibition, prevention, or destruction of the tumor cells upon expression of the nucleic acid sequence encoding the agent to form a producer cell line including the viral vector. The producer cells then are administered to the tumor, whereby the producer cells generate viral particles capable of transducing the tumor cells.

In a preferred embodiment, the viral vector is a retroviral or adenoviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus.

Retroviral vectors are useful as agents to mediate retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

These new genes have been incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

In one embodiment, the retroviral vector may be one of a series of vectors described in Bender, et al., *J. Virol.* 61:1639–1649 (1987), based on the N2 vector (Armentano, et al., *J. Virol.*, 61:1647–1650) containing a series of deletions and substitutions to reduce to an absolute minimum the homology between the vector and packaging systems. These changes have also reduced the likelihood that viral proteins would be expressed. In the first of these vectors, LNL-XHC, there was altered, by site-directed mutagenesis, the natural ATG start codon of gag to TAG, thereby eliminating unintended protein synthesis from that point.

In Moloney murine leukemia virus (MoMuLV), 5' to the authentic gag start, an open reading frame exists which permits expression of another glycosylated protein (pPr80$^{gag}$). Moloney murine sarcoma virus (MoMuSV) has alterations in this 5' region, including a frameshift and loss of glycosylation sites, which obviate potential expression of the amino terminus of pPr80$^{gag}$. Therefore, the vector LNL6 was made, which incorporated both the altered ATG of LNL-XHC and the 5' portion of MoMuSV. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller, et al., *Biotechniques,* 7:980–990, 1989).

The paramount need that must be satisfied by any gene transfer system for its application to gene therapy is safety. Safety is derived from the combination of vector genome structure together with the packaging system that is utilized for production of the infectious vector. Miller, et al. have developed the combination of the pPAM3 plasmid (the packaging-defective helper genome) for expression of retroviral structural proteins together with the LN vector series to make a vector packaging system where the generation of recombinant wild-type retrovirus is reduced to a minimum through the elimination of nearly all sites of recombination between the vector genome and the packaging-defective helper genome (i.e. LN with pPAM3).

In one embodiment, the retroviral vector may be a Moloney Murine Leukemia Virus of the LN series of vectors, such as those hereinabove mentioned, and described further in Bender, et al. (1987) and Miller, et al. (1989). Such vectors have a portion of the packaging signal derived from a mouse sarcoma virus, and a mutated gag initiation codon. The term "mutated" as used herein means that the gag initiation codon has been deleted or altered such that the gag protein or fragment or truncations thereof, are not expressed.

In another embodiment, the retroviral vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The vector includes one or more promoters. Suitable promoters which may be employed include, but are not limited to, the retroviral LTR; the SV40 promoter; and the human cytomegalovirus (CMV) promoter described in Miller, et al., *Biotechniques,* Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein, one embodiment employs a radiation responsive promoter to further turn on the thymidine kinase gene.

The vector then is employed to transduce a packaging cell line to form a producer cell line. Examples of packaging cells which may be transfected include, but are not limited to the PE501, PA317, Ψ2, Ψ-AM, PA12, T19-14X, VT-19-17-H2, ΨCRE, ΨCRIP, GP+E-86, GP+envAM12, and DAN cell lines. The vector containing the nucleic acid sequence encoding the agent which is capable of providing for the inhibition, prevention, or destruction of the growth of the tumor cells upon expression of the nucleic acid sequence encoding the agent may transduce the packaging cells through any means known in the art. Such means include, but are not limited to, electroporation, the use of liposomes, and $CaPO_4$ precipitation.

The producer cells then are administered directly to or adjacent to the tumor in an amount effective to inhibit, prevent, or destroy the growth of the tumor upon subsequent radation therapy. In general, the producer cells are administered in an amount tolerated by the patient, it is desirable to inject as many producer cells as possible. The exact amount of producer cells to be administered is dependent upon various factors, including but not limited to, the type of the tumor and the size of the tumor.

In general, the producer cells are administered directly to or adjacent to the tumor by injection. The producer cells are administered in combination with a pharmaceutically acceptable carrier suitable for administration to a patient. The carrier may be a liquid carrier such as, for example, a saline solution.

Upon administration of the producer cells to the tumor, the producer cells generate viral particles. The viral particles then transduce the surrounding tumor cells. Because tumor cells, and in particular cancerous tumor cells, in general are actively replicating cells, the retroviral particle would be integrated into and expressed preferentially or exclusively in the tumor cells as opposed to normal cells.

Tumors which may be treated in accordance with the present invention include malignant and non-malignant tumors. Malignant (including primary and metastatic) tumors which may be treated include, but are not limited to, those occurring in the adrenal glands; bladder; bone; breast; cervix; endocrine glands (including thyroid glands, the pituitary gland, and the pancreas); colon; rectum; heart; hematopoietic tissue; kidney; liver; lung; muscle; nervous system; brain; eye; oral cavity; pharynx; larynx; ovaries; penis; prostate; skin (including melanoma); testicles; thymus; and uterus. Examples of such tumors include apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, merkel cell, mucinous, non-small cell lung, oat cell, papillary, scirrhous, bronchiolar, bronchogenic, squamous cell, and transitional cell), plasmacytoma, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, mesenchymoma, mesonephroma, myosarcoma, ameloblastoma, cementoma, odontoma, teratoma, thymoma, throphoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, antiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's experimental, Kaposi's, and mast-cell), neoplasms and for other such cells.

According to the invention, the agent which is capable of providing for the inhibition, prevention, or destruction of the growth of the tumor cells upon expression of such agent is an activating gene.

Thus, upon transduction of the tumor cells with the activating gene, an interaction agent is administered to the host organism (human or animal). The interaction agent interacts with the negative selective marker in order to sensitize the transduced cells to the effects of radiation to prevent, inhibit, or destroy the growth of the tumor cells.

Activating genes which may be employed include factors which confer activity to nucleoside pyrimidine analogs which include but are not limited to, thymidine kinase, such as Herpes Simplex Virus thymidine kinase, cytomegalovirus thymidine kinase, and varicella-zoster virus thymidine kinase. These types of viral thymidine kinases will provide a second pathway to metabolise the interaction agents or precursors to radiation sensitizers refractory to end product inhibition.

In a preferred embodiment, the activating gene is a viral thymidine kinase selected from the group consisting of Herpes Simplex Virus thymidine kinase, related cytomegalovirus enzymes, and varicella-zoster virus thymidine kinase. When such viral kinases are employed, the interaction agent which can be used in addition to the radiation treatment preferably is selected from the group comprising nucleoside pyrimidine analogs such as 5-halogentated derivitives of deoxycytidine. Such interaction agents are utilized efficiently by the viral thymidine kinases as substrates, and thus their derivatives (or metabolites) are incorporated into the DNA of the tumor cells expressing the viral thymidine kinases, thereby resulting in increased sensitivity of the cells to the effects of radiation therapy.

The radiation precursor or interaction agent is administered in an amount effective to inhibit, prevent, or destroy the growth of the transduced tumor cells upon radiotherapy. The precurser or agents may be administered to the host in an amount of as much as strategically possible, traditionally this is in an amount of from about 200 to about 3000 mg/m$^2$/day, preferably in an amount of from about 500 to about 1200 mg/m$^2$/day for 7 to 14 days. The amount is limited only by traditional delivery mechanisms as the radiation precursors of the invention are safe and non toxic to normal cells. The agents or precursors are administered systemically, such as, for example, by intravenous administration, by parenteral administration, by intraperitoneal administration, or by intramuscular administration.

When producer cells or other expression media including an activating gene are administered to a tumor in vivo, metabolic cooperation a "bystander effect" will result, i.e., tumor cells which are not transduced with the nucleic acid sequence encoding the negative selective marker may be killed upon administration of the interaction agent and exposure to radiation therapy. Although the scope of the present invention is not intended to be limited to any theoretical reasoning, the transformed tumor cells may be producing a diffusible form of the negative selective marker that either acts extracellularly upon the interaction agent, or the negative selective marker (the viral tk, for example) is taken up by adjacent, non-transformed tumor cells, which then become susceptible to the action of the interaction agent. It also is possible that one or both of the negative selective marker and the interaction agent are communicated between tumor cells.

In a preferred embodiment, a packaging cell line is transduced with a retroviral vector, such as those hereinabove described, which includes the Herpes Simplex Virus thymidine kinase gene. The transduced packaging cells are administered in vivo to the tumor in an acceptable pharmaceutical carrier and in an amount effective to inhibit, prevent, or destroy the growth of the tumor. Upon administration of the producer cells to the tumor, the producer cells generate viral particles including a gene encoding the negative selective marker. Such viral particles transduce the adjacent tumor cells.

The human or animal host organism is then given an agent such as 5-halogenated derivitives of deoxycytidine (e.g. 5-bromodeoxycytidine or 5 iododeoxycytidine) which interacts with the Herpes Simplex Virus thymidine kinase to sensitize the transduced tumor cells to radiation. As hereinabove mentioned, a "bystander effect" may also occur, whereby non-transduced tumor cells also may be killed as well.

Transformation of tumor cells with Herpes Simplex Virus thymidine kinase and subsequent treatment with anti-viral agents such as gancyclovir has been previously accomplished and has proven to be operable in vivo both in animals and in humans. See "Gene Therapy for the Treatment of Recurrent Pediatric Malignant Astrocytomens With In Vivo Tumor Transduction with Herpes Simplex Thymidine Kinase Gene/Gancyclovir System", Raffel, C et al., *Human Gene Therapy* 5(7) p. 863–90, July 1994. Applicants herein propose an alternative or additional strategy for exploiting HSV-tk transduced cells by taking advantage of their ability to metabolize radiation precursors to active form.

The method of the present invention utilizing retroviruses is particularly useful when the targeted tumor is in or surrounded by a tissue made up of cells which are relatively quiescent mitotically, such as liver, skin, bone, muscle, bladder, prostate, kidney, adrenal, pancreas, heart, blood vessel and thyroid tissue, among others. The inventive approach also should be useful against tumors located in the subarachnoid space, in the peritoneum, and in the pleural cavity. In addition, tumors in organs the loss of which, in whole or part, is generally well-tolerated are preferred targets of a treatment according to the present invention such as the liver, for example.

Direct injection of the producer cells minimizes undesirable propagation of the virus in the body, especially when replication-competent retroviral vectors are used. Because most cells of the body express receptors for amphotropic retroviral vectors, any vector particle which escapes from the local environment of the tumor should immediately bind to another cell. Most cells are not in cycle, however, and therefore will not integrate the genes carried by the vector and will not express any genes which it contains. Thus, the proportion of potential target cells which are in cycle at the time of exposure will be small, and systemic toxic effects on normal tissues will be minimized.

In accordance with the present invention it is postulated that transduction of tumor cells with viral thymidine kinase can be exploited by introduction nucleoside analogs to sensitize the cells to radiation. This type of transformation procedure hereinabove described has been used exclusively to date with anti-herpetic agents such as acyclovir gancyclovir etc.

Without wishing to be bound by any theory, it is postulated that transformation with the Herpes thymidine kinase gene provides cells with a second route for metabolism of 5-halogenated analogs of deoxycytidine as shown in FIG. 1.

The Herpes simplex virus pyrimidine nucleoside kinase is both a thymidine kinase and a deoxycytidine kinase. In contrast, mammalian cells have a biochemically and genetically distinct thymidine kinase and deoxycytidine kinase respectively. 5-halogenated derivatives of deoxycytidine are thus selectively phosphorylated in HSV-tk containing cells since the analogs are analogs of both deoxycytidine (having a 4-$NH_2$ group) and of thymidine (having a 5-halogenated group with a VanderWaal radius similar to $CH_3$). Mammalian deoxycytidine kinase cannot readily phosphorylate these analogs (the Km values of 5-bromodeoxycytidine and 5-iododeoxycytidine with respect to mammalian deoxycytidine kinase is 2100 $\mu$M and 4000 $\mu$M respectively). Mammalian thymidine kinase, similarly, cannot phosphorylate BrDc or IdC. In contrast, the Km values for these analogs with respect to the Herpes pyrimidine nucleoside kinase is 2 $\mu$M, approximately the same value for thymidine.

Thus as shown in FIG. 1, in untransformed cells 5-halogenated derivatives of deoxycytidine are not phosphorylated to BrdUMP. Instead the route of phosphorylation requires deamination of BrdC to BrdU which is then phosphorylated by mammalian thymidine kinase to BrdUMP, and ultimately to BrdUTP which is incorporated into DNA increasing its susceptibility to radiation. Mammalian thymidine kinase, however is feed-back inhibited by IdUTP or BrdUTP, limiting the effects of BrdU or IdU as radiosensitizers.

According to the invention, in HSV-tk transformed cells an alternate pathway of metabolism (pathway B) is also present. BrdC or IdC is phosphorylated directly to BrdCMP by HSV-induced pyrimidine nucleoside kinase (HSV-tk) which is then converted to BrdUMP by deoxycytidylate deaminase. This enzyme as well as the higher kinases are elevated to high levels in tumor cells, See Maehara, Y et al, "Activities of Various Enzymes of Pyrimidine Nucleoside and DNA Synthesis in Normal and Neoplastic Cells", Gann. 73:289–298 (1982); Giusti B, et al, "Deoxycytidylate Deaminase in Normal and Neoplastic Tissue", *Enzym. Biol. Clin.* 11:375–383 (1970) both of which disclose in vitro assays for the presence of these enzymes and which are herein incorporated by reference. 5-BrdUMP and 5-IdUMP are then phosphorylated by the higher kinases which are elevated in tumors are incorporated into DNA and result in radiosensitization to X-rays, γ-rays, β-rays, ultraviolet light, near ultraviolet light neutrons and other sources of radiation including, for example π-mesons.

Transformed cells will have two doses of tk, one mammalian, and one HSV, which may alone enhance phosphorylation of IdU or BrdU. In addition, the Herpes tk is resistant to end product inhibition by IdUTP or BrdUTP. IdUTP or BrdUTP are capable of shutting off mammalian tk, thereby limiting the effectiveness of IdU or BrdU as a radiosensitizer. In contrast, with an end-product-inhibitor-refractory tk, IdU and BrdU can be phosphorylated without the limitations of feed back inhibition.

For a further selective effect, an inhibitor of mammalian cytidine deaminase (e.g. tetrahydrouridine ($H_4U$) can be administered. As such, 5-halogenated analogs of deoxycytidine will not be toxic or radiosensitizing to mammalian cells and will only be activated by cells carrying the nucleotide sequence encoding and expressing Herpes pyrimidine nucleoside kinase (HSV-tk). Tetrahydrouridine has been shown to be safe and non toxic in mammalian cells. Cooper and Greer, "The Effect of Inhibition of Cytidine Deaminase by Tetrahydrouridine on the Utilization of Deoxycytidine and 5-bromodeoxycytidine for DNA Synthesis", *Mol. Pharm.* 9:698–703 (1973).

To enhance selectivity and decrease toxicity, deoxycytidine could be co-administered. Deoxycytidine has a low Km (2$\mu$M) with respect to mammalian deoxycytidine kinase but a high Km with respect to HSV-tk (500 $\mu$M). Thus deoxycytidine will selectively antagonize any general toxicity which may result from the anticipated by possible phosphorylation of BrdC and IdC (which have high Kms with respect to mammalian deoxycytidine kinase and a low Km with respect to HSV-tk) as as stated above. In contrast, deoxycytidine will not affect the activation of BrdC or IdC in Hs-tk transfected cells.

Previous attempts at killing tumor or cancer cells with HSV-tk or other viral thymidine kinases have focused exclusively on anti-herpetic agents such as gancyclovir, acyclovir, 1-2-dioxy-2-fluoro-β-D-arabinofuranosil-5-iodouracil (FIAV).

The invention will now be described with respect to the following examples; however, the scope of the present invention is not intended to be limited thereby.

EXAMPLE 1

A375 Melanoma Cells Sensitization With HSV-TK and Iododeoxycytidine (IdC)

Ovarian cancer is the most common cause of gynacologic cancer death in women in the United States. Approximately 24,000 American women will be diagnosed with epithelial ovarian cancer and 13,600 of those patients will die. Patients usually present with advance staged disease and although the majority respond well to therapy, about ⅔ relapse often with disease confined to the abdomen. In this situation, salvage chemotherapy may induce some patients into remission and palliation is possible but long term survival is rare. A number of salvage approaches with chemotherapy have used the direct instillation of drug into the peritoneal cavity of women with persistent or recurrent disease, because this tumor often remains localized to the abdomen in the early stages of relapse.

Radiation therapy has also been used effectively both for the initial therapy of low stage ovarian cancer and for treatment of persistent recurrent disease either alone or with chemotherapy, but is unfortunately associated with significant toxicity to normal abdominal tissues. The halogenated pyrimidines are nucleoside analogues that have demonstrated activity in potentiating X-irradiation induced cytotoxcity. These findings lead to clinical trials of the thymidine analogue, bromodeoxyuridine. Unfortunately, these compounds have demonstrated little selective toxicity and often have significant side effects because of sensitizing effects in normal tissues especially in bone marrow and gastrointestinal tissues.

Figure 2:
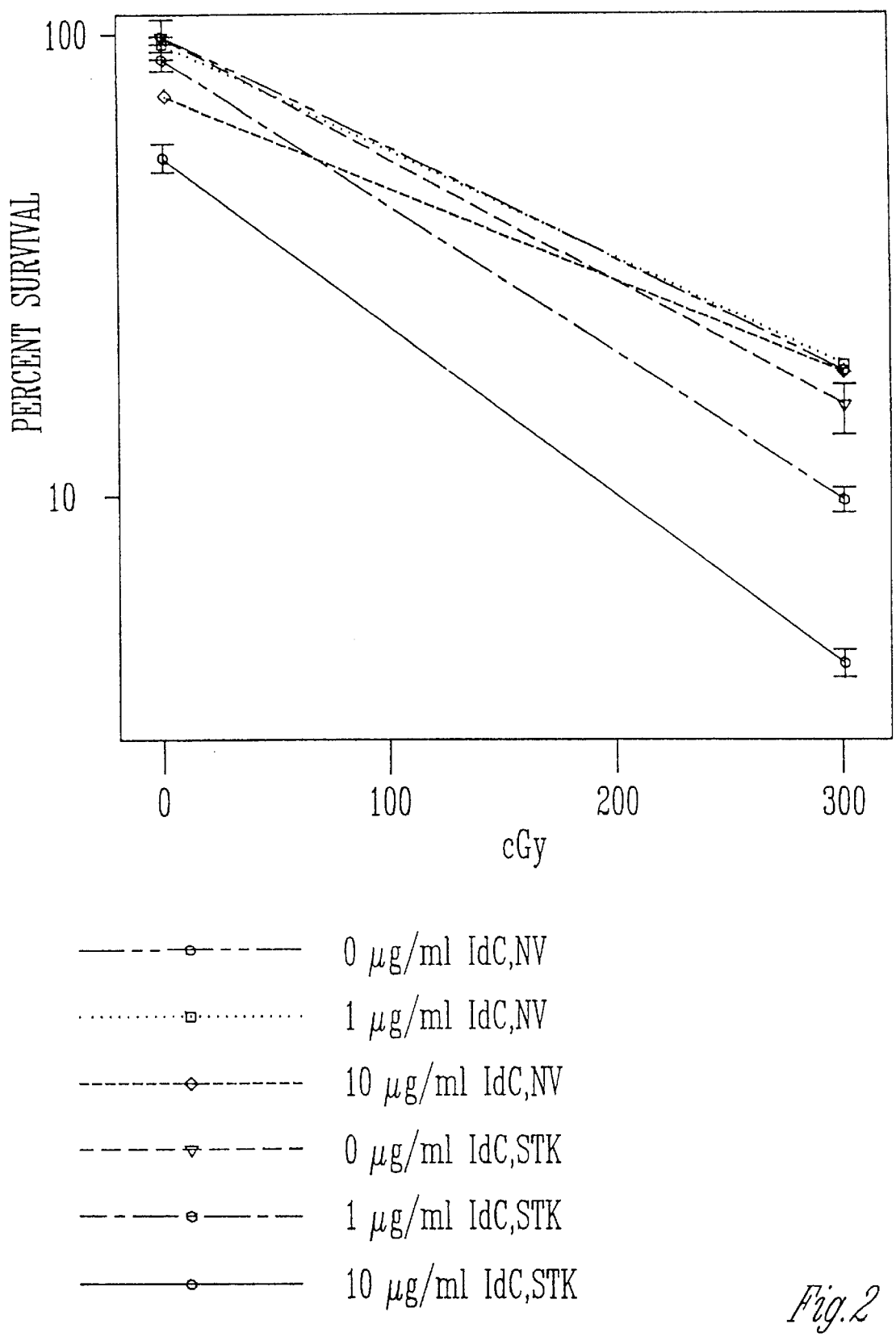
FIG. 2 is a graph depicting the results of cells treated in vitro by the method of the invention. Cells were transformed with the STK vector and then treated with 5-iododeoxycytidine. As can be seen, Cells treated in this manner exhibited less than 10% survival compared with approximately 50% survival for nontransformed cells treated with radiation.

For this example, a vector, termed LNSTK was kindly provided by F. Moolten which contained the HS-tk gene driven by the SV40 early promoter. Other transformation vectors containing the HS-tk retroviral vector such as the LTKOSN.2 vector by the Human Gene Therapy Research Institute (Des Moines, Iowa) are commercially available. Another such vector is the G1TkSvNa vector by Genetic Therapy Inc., Gaithersburg, MD. A human A375 melanoma cell line was used because of its ease of growth and rapid colony formation in a clonogenic assay. The survival of A375NV (no vector) and A375TK (transduced with LNStk vector) after 30 GY of gamma-radiation with 0,1, or 10 g/ml IdC is shown in FIG. 2.

$1 \times 10^x$ cells were plated in a 100 cm$^2$ tissue culture dish in free media. The next day drug was added in the appropriate concentration. 48 hours later the cells were irradiated with 30 GY from a 250 KV X-ray machine as a single dose. The cells were then trypsinized and replated at between $2.5 \times 10^2$ and $1 \times 10^6$ cells per plate in triplicate for each data point. After twelve days the cells were fixed, stained and macroscopic colonies containing $\leq 50$ cells were counted. Measurements in the graph were corrected for plating efficiency. As can be seen in FIG. 2, non irradiated A375 NV and A375 tk cells had 73% and 54% survival respectively when incubated with 10 μg/ml of IdC compared to non-irradiated control cells not preincubated with drug. Irradiated A375 NV preincubated with 0,1 or 10 μg/ml of IdC had 18.6, 19.3 and 18.3 percent survival respectively. Irradiated A375 tk cells preincubated with 0,1, or 10 μg/ml of IdC had 15.7, 9.9 and 4.4 percent survival respectively. These results show selective radiation enhancement of the LNS-tk retroviral transduced cells over non-transduced. At the IdC concentrations used little toxicity to the tumor cells was noted and no degree radiation potentiation was seen in the absence of the HS-tk gene. These results demonstrate that the HS-tk gene can induce very specific and selected toxicity of the gene-altered cells.

EXAMPLE 2

A375 Melanoma Cell Sensitization With HSV-tk and Bromodeoxycytidine (BrdC)

Figure 3:
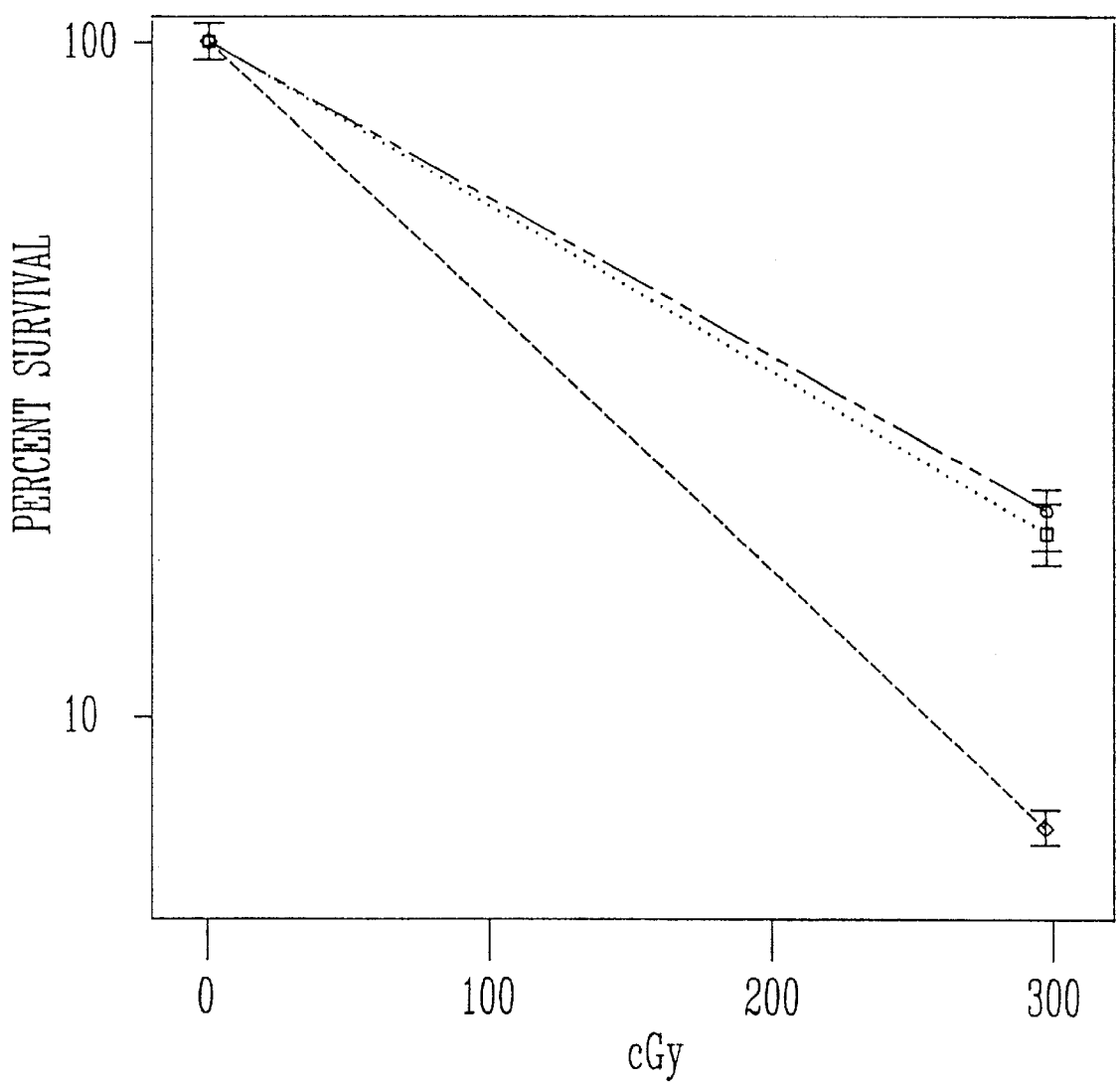
FIG. 3 is a graph depicting the results of cells treated as in FIG. 2 with 5-bromodeoxycytidine. A similar reduction in cells survival to less than 10% was seen for cells transformed with the STK vector.

In FIG. 3 another experiment is shown, design similar to Example 1. This experiment compared radio sensitivity of A375 NV and A375 tk cells after preincubation with 10 μg/ml of BrdC for 48 hours before X-ray exposure. The graph is plotted to demonstrate the enhancement effect after adjusting the survival rates for toxicity induced by drug alone in the absence of radiation. Survival percentages for cells incubated with 10 μg of BrdC and then irradiated with 30 Gy were divided by the survival fraction of cells incubated with 10 μg/ml of BrdC and then mock irradiated.

As can be seen the survival (before adjustment) for A375 tk cells preincubated with 10 μg/ml of BrdC was 33% and 2.3% for nonirradiated and irradiated groups respectively. Dividing irradiated cell survival (2.3%) by the nonirradiated surviving fraction (0.33%) gives the adjusted survival of 6.9%. This allows a better comparison to determine the true enhancement due to the interaction of the HS-tk gene and radiation and shows the survival of irradiated A375 tk cells had a survival of 6.9% while the adjusted value for A375 NV cells incubated with drug was 9%. This implies that a more than additive radiation enhancement effect occurs. This data represents the first use of gene therapy to enhance tumor radiosensitivity. While not wishing to be bound by any theory, it is hypothesized that HS-tk transduced tumor cells are able to additionally sensitize nontransduced cells in their vicinity through a bystander effect. It is thought that these nucleoside analogues show metabolic cooperation in an analogous manner as has been described before gancyclovir.

Figure 4:
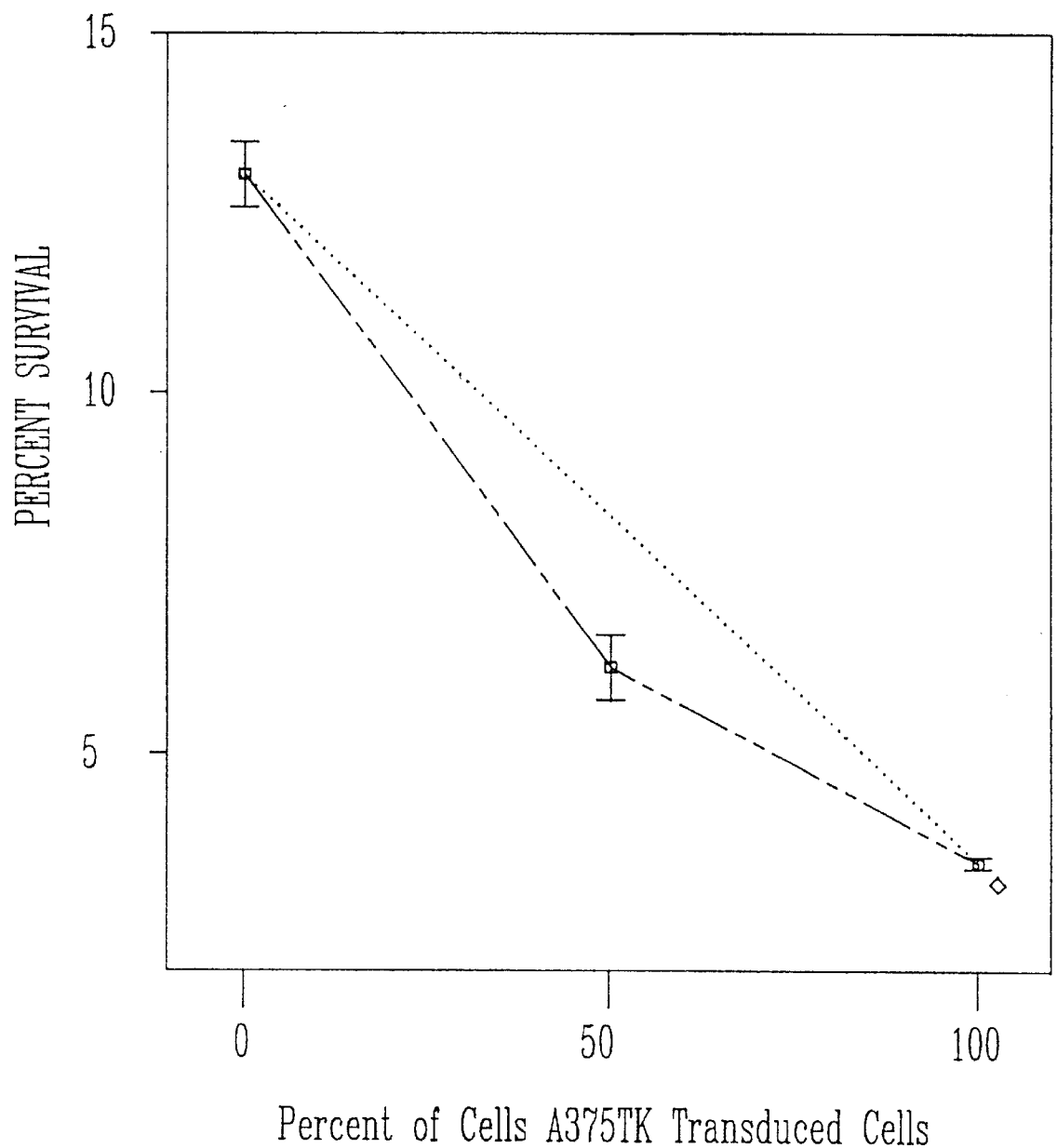
FIG. 4 demonstrates the additive effect of cells treated by the method of the invention. The expected percent survival calculated from data is significantly larger that the actual percent survival experienced indicated a bystander effect.

Without wishing to be bound by any theory it is hypothesized that HSV-tk transduced tumor cells are able to sensitize non transduced tumor cells in their vicinity through a bystander effect via metabolic cooperation. Specifically, cells that are not transduced with HS-tk gene can also be sensitized to radiation. FIG. 4 shows the result of a clonogenic assay conducted with 100% A375 tk cells, a mixture of 50% A375 NV and 50% A375 HS-tk cells and 100% A375 NV cells. These cells were plated at a density of $3 \times 10^6$ cells per 100 cm$^2$ tissue culture dish the afternoon prior to adding 10 μg/ml BrdC to the media. At this concentration the cells are about 90% confluent and therefore exhibit a large amount of cell to cell contact with adjacent cells in the culture. FIG. 4 shows the results of the first experiment of this design. The expected line represents a theoretical cell kill curve if only tk transduced cells exhibit a radiation enhancement effect from preincubation with BrdC. A375 tk and A375 NV cells preincubated with 10 μg/ml BrdC treated with 30 Gy demonstrated 3.5% and 13.1% survival respectively. The "expected" survival after BrdC exposure for a mixture containing 50% A375 tk and 50% A375 NV would be one-half the survival for irradiated A375 tk cells alone, plus half the survival for irradiated A375 NV cells alone (0.5) (3.5%)+(0.5) (13.1%) (=8.3%). In contrast the experimentally obtained survival for this mixture of cells when plated together at high density was only 6.2%. This suggests that the potentiation effect also occurs in non-transduced cells when incubated with drug in the presence of HS-tk transduced cells.

Table 1 shows the plating scheme for the in vitro clonogenic assay of HS-tk induced radio sensitivity.

| | | | | | | # CELLS/PLATE | | | |
|---|---|---|---|---|---|---|---|---|---|
| GROUP | cGy | DRUG | [DRUG] | TIME | | | | | |
| IGROV | | no vector (NV) | | | $2.5 \times 10^2$ | $1 \times 10^3$ | $1 \times 10^4$ | $1 \times 10^5$ | $1 \times 10^6$ |
| A | 0 | None | | | X | | | | |
| B | 0 | BrdC | 10 μg/ml | 24 h. | X | X | | | |
| C | 200 | None | | | X | X | | | |
| D | 200 | BrdC | 10 μg/ml | 24 h. | | X | X | | |
| E | 400 | None | | | | X | X | X | |
| F | 400 | BrdC | 10 μg/ml | 24 h. | | X | X | X | |
| G | 700 | None | | | | | X | X | X |
| H | 700 | BrdC | 10 μg/ml | 24 h. | | | X | X | X |
| I | 1000 | None | | | | | X | X | X |

-continued

Plating scheme for in vitro clonogenic assay of HStk induced radiosensitivity

| GROUP | cGy | DRUG | [DRUG] | TIME | # CELLS/PLATE | | | | |
|---|---|---|---|---|---|---|---|---|---|
| | | | | | $2.5 \times 10^2$ | $1 \times 10^3$ | $1 \times 10^4$ | $1 \times 10^5$ | $1 \times 10^6$ |
| IGROV | | no vector (NV) | | | | | | | |
| J | 1000 | BrdC | 10 μg/ml | 24 h. | | | X | X | X |
| IGROV exposed to LTKOSN supernate | | | | | | | | | |
| AA | 0 | None | | | X | | | | |
| BB | 0 | BrdC | 10 μg/ml | 24 h. | X | X | | | |
| CC | 200 | None | | | X | X | | | |
| DD | 200 | BrdC | 10 μg/ml | 24 h. | X | X | | | |
| EE | 400 | None | | | | X | X | X | |
| FF | 400 | BrdC | 10 μg/ml | 24 h. | | X | X | X | |
| GG | 700 | None | | | | | X | X | X |
| HH | 700 | BrdC | 10 μg/ml | 24 h. | | | X | X | X |
| II | 1000 | None | | | | | X | X | X |
| JJ | 1000 | BrdC | 10 μg/ml | 24 h. | | | X | X | X |

Cells exposed to supernate transfer from PA317 or LTKOSN/PA317 VPC twice daily for two days. Cells were then replated on day 3. Drug added 24 hours later on day 4. Cells were harvested and plated in triplicate. Colonies were fixed, stained, and counted from 10 to 14 days later.

EXAMPLE 3 (PROPHETIC)

In Vivo Sensitization with BrdC or IdC and HSV-tk

A proposed in vivo scheme for the invention is as follows:

One animal model, Syngeneic murine MCA 205 tumor cells (obtained from ATCC) would be mixed and injected subcutaneously into the anterior abdominal wall of C57BI/6 mice. This assay can provide a rapid and inexpensive model to test new retroviral vectors and provides quantitative data in a relatively short period of time. Animals would be injected with mixtures of 205 cells transduced with an HS-tk containing retroviral vector. Animals would be injected into the anterior abdominal wall in each group. The 205 subcutaneous model, the syngeneic MC 38 IP model and the human ovarian cancer xenografts and athymic nude mice are all animal models which can be used to demonstrate applicants' invention.

The MC 38 murine syngeneic model is as follows. Mice would be anesthetized with ketamine/xylazine solution and placed in a lead shield with an open groove through which the tumor was locally irradiated under air-breathing conditions. An initial pilot experiment would be conducted to determine the dose of radiation that provided a growth delay of about 6–8 days compared to nonirradiated controls. When tumors had reached an average of 8 mm in diameter the mice would be randomly assigned to a treatment group. The quantitative effects of treatment on tumor regrowth will be expressed as absolute growth delay (AGD) expressed as the number of days for tumors to reach 10 mm over the number of days for the untreated control tumors to reach 10 mm. The net growth delay (NGD) from the combination of prodrug and HS-tk gene would be determined by the time to reach 10 mm in animals irradiated and receiving drug minus the time to reach 10 mm in animals that received the drug alone. The determination for thymidine replacement by IdU and BrDU has been previously described. Mitchell et al, Differing Sensitivity To Fluorescent Light In Chinese Hamster Ovarian Cells Containing Equally Incorporated Quantities Of BUDR and IUDR., Int.J.Radiat.Oncol.Biol.Phys. 1984, p. 1447–1451 incorporated herein by reference. External beam experiments with intraperitoneal tumor already transduced with LTKOSN compared to nontransduced tumors. One experiment could be conducted with Mc 38 tumors. Animals were treated with whole abdominal irradiation with a Clinac 250 ku X-ray machine. Mc 38 adenocarcinoma cells proliferate and cause the demise of C57BI/6 mice more rapidly (usually around 3–4 weeks after inoculating $1 \times 10^5$ cells) then human tumor xenografts in nude mice (60 to 120 days depending on cell line after inoculation of $1 \times 10^7$ cells). The drug dosage used with be established by the MC 38 subcutaneous model experiments.

TABLE 2

In vivo Radiation Sensitization by LTKOSN and BrdC

| Group | Tumor | Drug | cGy | No. Mice |
|---|---|---|---|---|
| A | MC 38 NV | None | None | 10 |
| B | MC 38 NV | BrdC | None | 10 |
| C | MC 38 NV | None | 0.1X | 10 |
| D | MC 38 NV | BrdC | 0.3X | 10 |
| E | MC 38 NV | None | 0.1X | 10 |
| F | MC 38 NV | BrdC | 0.3X | 10 |
| G | MC 38 TK | None | None | 10 |
| H | MC 38 TK | BdCyd | None | 10 |
| I | MC 38 TK | None | XX | 10 |
| J | MC 38 TK | BdCyd | XX | 10 |
| K | MC 38 TK | None | XX | 10 |
| L | MC 38 TK | BrdC | XX | 10 |

MC 38 cells ($1 \times 10^5$) in 100 ml HBSS IGROV will be injected intraperitoneally on day 1. Tumor will be inoculated on day 1.

Specific cell lines may demonstrate less selectivity of these agents especially if they contain elevated cytidine deaminase (CD) activity which could convert BrdC or IdC to their uridine analogues. This problem could be circumvented by blocking the activity of mammalian CD by a deaminase inhibitor such as Tetrahydrouridine. This would prevent conversion within normal tissues to the Urd derivatives that could sensitize the normal tissues. Another strategy to circumvent the problem would be to block de novo pathway synthesis using 5-Fluorouridine or other F-pyrimidine analogs.

What is claimed is:

1. A method of selectively targeting and killing tumor cells and those cells subject to the bystander effect comprising:

implanting a retrovirus producer cells into or adjacent to said tumor cells, wherein the retrovirus comprises operatively linked to a promoter a gene encoding a viral thymidine kinase; such that said tumor cells become transduced by said retrovirus and express said viral thymidine kinase gene;

administering to said transduced tumor cells a 5-halogenated derivative of deoxycytidine; and exposing said tumor cells to radiation therapy, wherein growth of the tumor cells is thereby inhibited.

2. The method of claim 1, wherein said viral thymidine kinase is a herpes or varicella thymidine kinase.

3. The method of claim 1, wherein said viral thymidine kinase is Herpes Simplex Virus thymidine kinase.

4. The method of claim 1, wherein said 5-halogenated deoxycytidine is selected from the group consisting of 5-bromodeoxycytidine and 5-iododeoxycytidine.

5. The method of claim 1, wherein said implantation is by the direct injection of said producer cells lines at or adjacent to said tumor cells.

6. A method of conferring radiation sensitivity to tumor cells comprising:

directly implanting a retrovirus producer cell line into or adjacent to a tumor, wherein said producer cells produce a replication defective retrovirus comprising a gene encoding a viral thymidine kinase operatively linked to a promoter such that the cells of the tumor are transformed by the retrovirus and express said gene encoding a viral thymidine kinase;

administering a 5-halogenated pyrimidine derivative by a route and in an amount effective for said 5-halogenated pyrimidine to sensitize said tumor cells and tumor cells subject to a bystander effect to the effects of radiation; and exposing the sensitized cells to radiation sufficient to inhibit the growth of sensitized cells.

7. The method of claim 6, wherein said viral thymidine kinase is Herpes Simplex Virus thymidine kinase.

8. The method of claim 6 wherein, said 5-halogenated pyrimidine derivative is a 5-halogenated deoxycytidine derivative.

9. The method of claim 8 wherein, said 5-halogenated deoxycytidine derivative is selected from the group consisting of 5-bromodeoxycytidine and 5-iododeoxycytidine.

10. The method of claim 6 wherein, said delivery of said vector comprises direct injection of said producer cell line.

11. A process for sensitizing tumor cells in a mammal to radiation, comprising directly administering into or adjacent to a tumor, retrovirus producer cells, wherein said producer cells produce a replication defective retrovirus comprising a gene encoding a viral thymidine kinase operatively linked to a promoter;

expressing said gene in the cells of said tumor;

administering 5-bromodeoxyuridine triphosphate to said tumor cells such that 5-bromodeoxyuridine monophosphate is produced in an amount effective to sensitize said tumor cells to the effects of radiation; and exposing the sensitized cells to radiation sufficient to inhibit the growth of sensitized cells, wherein the growth of said tumor is thereby inhibited.

12. A method of selectively targeting and killing tumor cells and those cells subject to the bystander effect comprising:

directly administering an adenoviral vector comprising a gene encoding a viral thymidine kinase operably linked to a promoter to a tumor, such that the cells of said tumor become infected by said retrovirus and express said viral thymidine kinase gene;

administering to said transduced tumor cells a 5-halogenated derivative of deoxycytidine; and exposing said tumor cells to radiation therapy, wherein growth of the tumor cells is thereby inhibited.

13. An isolated mammalian tumor cell sensitized to radiation prepared by the method comprising the steps of:

(a) transforming mammalian tumor cells with a polynucleotide sequence which encodes a viral thymidine kinase; and (b) introducing to said transformed mammalian tumor cells a 5-halogenated derivative of deoxycytidine.

* * * * *